United States Patent [19]

Vogler et al.

[11] Patent Number: 5,257,633
[45] Date of Patent: Nov. 2, 1993

[54] SURFACE MODIFIED BLOOD COLLECTION TUBES

[75] Inventors: Erwin A. Vogler, Newhill; Garry R. Harper, Raleigh, both of N.C.

[73] Assignee: Becton, Dickinson and Company, Franklin Lakes, N.J.

[21] Appl. No.: 903,111

[22] Filed: Jun. 23, 1992

[51] Int. Cl.⁵ .............................................. A61B 5/00
[52] U.S. Cl. .................................. 128/763; 73/864.01
[58] Field of Search ............... 128/760, 763, 766, 770, 128/771; 73/864, 864.01, 864.73, 864.71

[56] References Cited

U.S. PATENT DOCUMENTS

| 4,188,426 | 2/1980 | Auerbach | 427/40 |
| 4,967,763 | 11/1990 | Nugent et al. | 128/763 |

FOREIGN PATENT DOCUMENTS

| 000341587 | 11/1989 | European Pat. Off. | 128/760 |
| 2435190 | 2/1975 | Fed. Rep. of Germany | 128/760 |
| 0067936 | 4/1984 | Japan | 128/760 |
| 3063569 | 3/1991 | Japan | 128/760 |
| 3218736 | 9/1991 | Japan | 128/760 |

OTHER PUBLICATIONS

Characterization of Hydrophobicity Gradients Prepared by Means of Radio Frequency Plasma Discharge, *Biomaterials*, 11, 32, (1990).

Protein and Detergent Interaction Phenomena on Solid Surfaces with Gradients in Chemical Composition, *Advances in Colloid and Interface Science*, 32, 317, (1990).

Primary Examiner—Max Hindenburg
Attorney, Agent, or Firm—Richard E. Brown

[57] ABSTRACT

A glass or plastic article, preferably a blood collection tube, has two or more surface regions of different surface chemistry. One region is substantially glass-like and another region is substantially plastic-like. If the tube is glass, a region of the tube adjacent the tube bottom is plastic-like. If the tube is plastic, a region of the tube adjacent the mouth of the tube is be glass-like.

13 Claims, 2 Drawing Sheets

SURFACE MODIFIED BLOOD COLLECTION TUBES

BACKGROUND OF INVENTION

1. Field of the Invention

This invention relates to medical devices and more particularly relates to a blood collection tube having surface regions of different chemistry.

2. Background

Blood samples are routinely taken in evacuated tubes, such as glass VACUTAINER TM tubes (Becton, Dickinson and Company). One end of a double-ended needle is inserted into a patient's vein. The other end of the needle then punctures a septum covering the open end of the VACUTAINER TM tube so that the vacuum in the tube draws the blood sample through the needle into the tube. Using this technique a plurality of samples can be taken using a single needle puncture of the skin.

Plastic tubes have also been proposed for blood collection. Plastic offers a number of advantages over glass, such as lower breakage, less weight in shipment, and easier disposal by incineration.

During sample collection, the blood comes into contact with the interior surface of the collection tube. The nature of the blood surface interaction is complex. For example, the blood clotting cascade is activated by contact of the blood with a wettable glass surface and the formed clot does not adhere to the glass, making it easy to separate clot from blood plasma by centrifugation. However, because the clot is non-adherent, it is subject to resuspension in part or whole into the plasma layer during handling or transportation. Thus, in glass tubes, the same surface properties that lead to easy separation of clot from the serum also allow the clot to move freely in the tube.

Plastic tubes generally have a nonwettable surface and do not activate the clotting process efficiently. Clots formed in these tubes may be quite gelatinous relative to those in glass. These gelatinous clots adhere tenaciously to plastic surfaces and do not allow for clean separation of serum from clot in conventional hematological centrifuges. However, the adherent clot is not easily disrupted by ordinary handling procedures. Thus, although serum and clot do not separate cleanly in plastic, the clot adheres to the plastic surface, and its mechanical stability is a positive feature not available in glass tubes.

Thus, the ideal blood collection tube for serum separation would exhibit both glass like and plastic like surface activity. In the present disclosure, the term glass-like is used to describe a surface which is substantially hydrophilic, which is wettable by aqueous liquids, which initiates clot formation and which is non adherent to the formed clot. The term plastic like is used to describe a surface which is substantially hydrophobic, substantially nonwettable by aqueous liquids, and which does not initiate clot formation to any significant degree, but which is highly adherent to clot material.

Various methods have been proposed for modification of glass and plastic surfaces. In one method, plastic surfaces are coated with a detergent material to render them more glass-like. This approach has the disadvantage of adding a soluble foreign material which contaminates the serum and may interfere with subsequent blood analysis.

In U. S. Pat. No. 4,967,763 to Nugent et al., plastic microcollection tubes are treated with an oxidative plasma to render the surface more hydrophilic, to achieve faster blood flow and to reduce blood hangup. Conversely, it is known to treat glass surfaces with a plasma to deposit a layer of hydrophobic plastic material. This technology is exemplified in U. S. Pat. No. 4,188,426 to Auerbach wherein a fluorine-containing layer is plasma deposited on a variety of surfaces, including plastic and glass. In these approaches, the entire interior surface of the tube is substantially modified to interconvert glass-like and plastic like surfaces and thus does not provide surface chemistry having dual functionality for blood collection. Formation of a hydrophobicity gradient on a polydimethylsiloxane film is taught by Golander et al. in *Biomaterials* 11,32 (1990). The film surface is exposed to an oxygen plasma generated in a planar diode system for various lengths of time as regulated by a cover movably positioned between the plasma and the polymeric surface.

Wettability gradients are formed on silicon plates by Elwing et al. in *Advances in Colloid and Interface Science*, 32,317 (1990). The gradients are formed by diffusion-induced silylation using dichlorodimethyl silane.

There is a need in the art of blood collection for a tube which promotes clot formation, permits clean separation of clot from serum and enhances strong adherence of the formed clot to minimize mechanical remixing of clot material with serum. The present invention fulfills this need.

SUMMARY OF THE INVENTION

An article includes a wall which has a wall surface having a plurality of surface regions which have different surface chemistries. At least one of the regions is substantially plastic-like and at least one of the regions is substantially glass-like.

The preferred article has an open end, a closed end, a wall and a wall surface. The wall, which preferably is continuous, includes a side wall and a bottom wall. The most preferred article is a tube which may be glass or plastic.

When the article is glass, one surface region is the native glass surface and a second region is the glass surface modified to be plastic-like. For this embodiment of the invention, the surface modified to be plastic like may preferably be adjacent the bottom wall and may include the bottom wall. The native glass surface is preferably adjacent the open end of the tube.

The plastic tube of the invention has a surface region which may be the native plastic surface and a surface region modified to be glass-like. For this embodiment of the invention, the region modified to be glass-like may preferably be adjacent the open end of the tube, and the native plastic surface region may preferably be adjacent to the bottom wall and may include the bottom wall.

Thus the article of the invention has two distinctly different kinds of surface properties which provide a dual clinical functionality. In blood collection tubes, the glass-like surface promotes clotting and provides a nonadherent surface to the formed blood clots. On the other hand, the blood clots adhere strongly to the plastic like surface region. When a blood sample taken in the tube of the invention is centrifuged, the blood clots at the glass-like region and the clot flows, pellets and adheres to the plastic-like region. A clear serum layer forms above the clot with no fibrin rings and strands suspended in the serum or adhering to the upper region of the tube. The strong adherence of the clot to the plastic like region prevents mechanical remixing of clot and serum when the centrifuged tube is handled or transported. The location and size of the different regions is easily predetermined by the treatment process so that the total volume occupied by clot and serum within the tube can be controlled by the location of the interface between the regions.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described and illustrated. The scope of the invention will be measured by the appended claims and their equivalents.

In accordance with the present invention, an article surface, preferably a continuous surface, is modified to have two or more regions of different chemistry. Regions of different surface chemistry may be formed on a variety of glass or plastic articles, such as films, plates, flasks, bottles, vials and dishes. The preferred article geometry is a tube, preferably a tube with one closed end.

The tube may be combined with a septum over the open end and may be evacuated. Evacuated tubes for blood collection are standard in the art as, for example VACUTAINER TM brand tubes (Becton, Dickinson and Company).

The invention will be described in detail for a tube with the understanding that any other article may be treated to have dual surface chemistry regions by the methods described.

The tube of the invention may be glass or plastic and may be of any shape or size. The preferred tube may be cylindrical and may be about 25-250, preferably about 75-100 mm long and 10-20 mm in diameter.

When the tube is glass, a plastic-like surface region may be introduced to a portion of the inside wall. When the tube is plastic, a glass-like surface region may be introduced to a portion of the inside wall.

Figure 1:
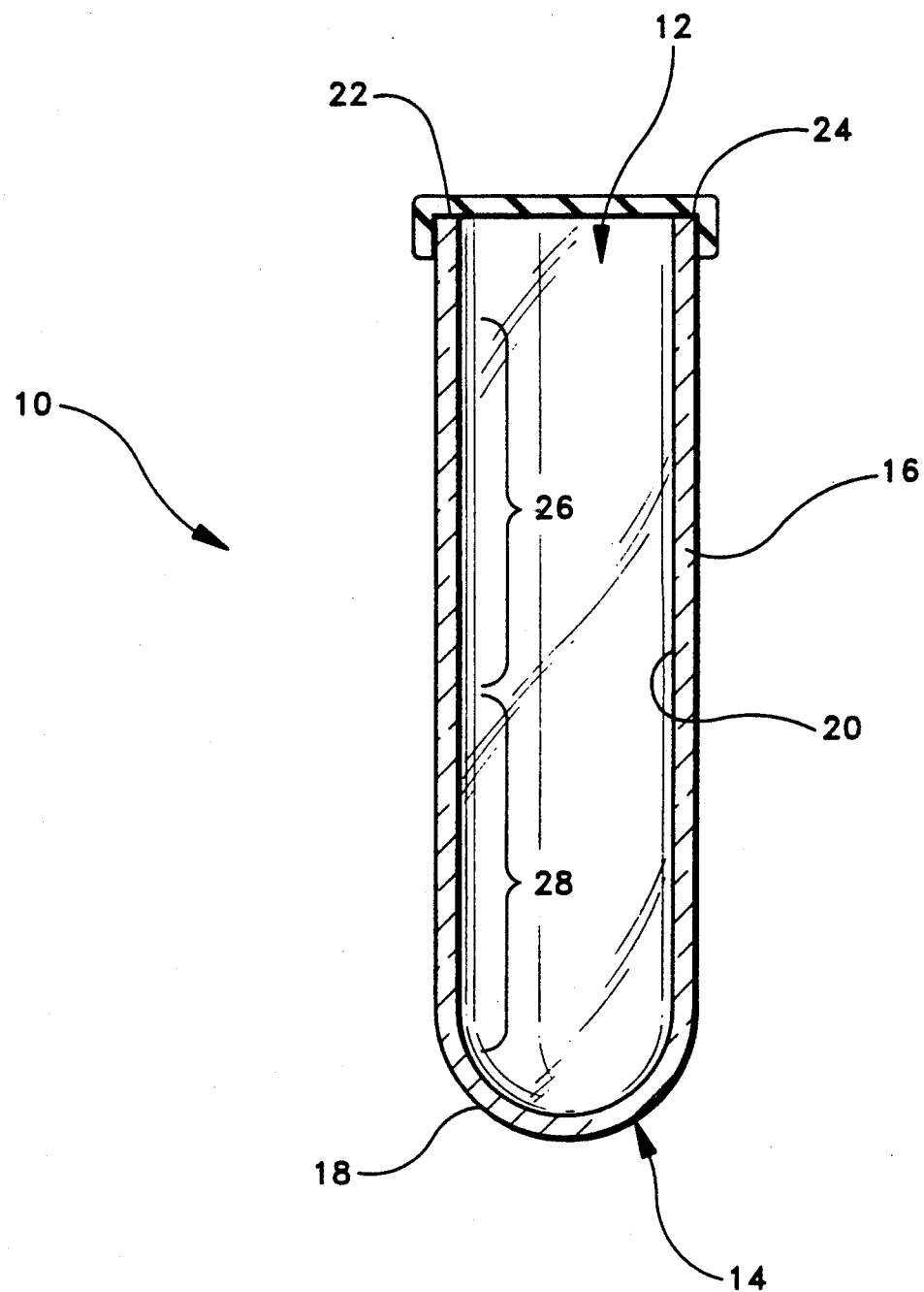
FIG. 1 illustrates the preferred tube of the invention and shows two regions of different surface chemistry.
Figure 2:
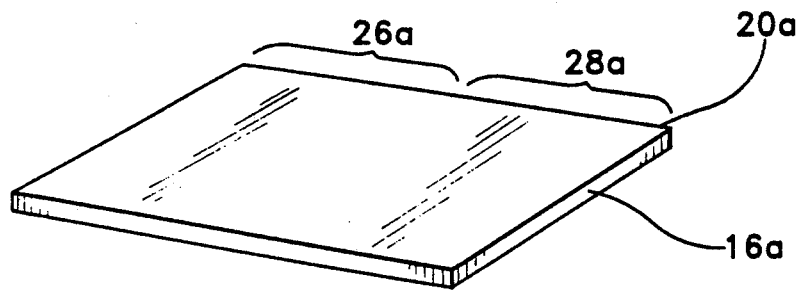
FIGS. 2-5 illustrate other embodiments of the article of the invention.
Figure 3:
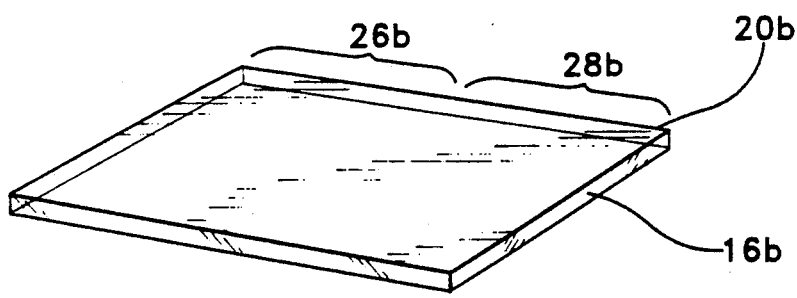
Figure 4:
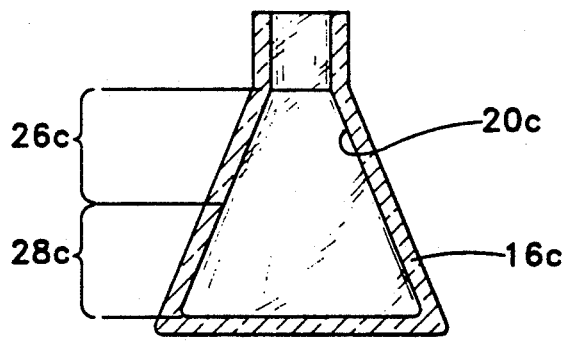
Figure 5:
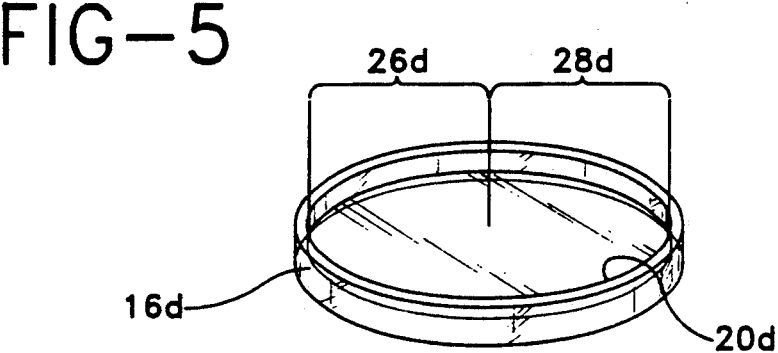

The tube of the invention will now be further described with the aid of the FIG. 1. A typical tube 10 of the invention has an open end 12, a closed end 14, a side wall 16 and a bottom wall 18. Walls 16 and 18 define an inside wall surface 20 which extends continuously from the top portions 22 and 24 of side wall 16. Wall surface 20 includes a region 26 adjacent the open end of the tube and a region 28 adjacent bottom wall 18 and optionally including the portion of inside wall 20 defined by bottom wall 18. Open end 12 of tube 10 may optionally be covered with a conventional puncturable septum.

FIGS. 2-5 illustrate a plastic sheet, glass plate, flask and dish respectively as exemplary of other embodiments of the article of the invention. In FIGS. 2-5, elements identical or substantially similar to elements described in FIG. 1 are given the same reference number followed by a letter suffix.

In accordance with the invention, it has been found that a glass tube may be treated with a reagent which renders the treated portion of the tube plastic like. The reagent may be a polymer. For example, a surface region of a glass tube may be rendered plastic like by dip coating a solution of a polymer in a volatile solvent on the surface and subsequently evaporating the solvent. Suitable polymers for this embodiment of the invention are polyethylene, polystyrene, polyvinyl chloride, polysiloxane and polytetrafluoroethylene. Suitable solvents are chloroform, dimethyl formamide, dimethylsulfoxide, dimethylacetamide and the like.

Alternatively, a monomer may be coated onto the region to be rendered plastic like and the monomer polymerized in situ. For example, the monomer, optionally in an inert solvent, can be polymerized by treatment with ultraviolet light so that, after evaporation of the solvent, a layer of polymer coating remains on the region.

Preferred reagents are silylation reagents, such as, for example, trimethylchlorosilane, methyldimethoxychlorosilane and chloromethyldimethylethoxysilane. The most preferred reagents are chlorosilanes having long chain alkyl substituents such as tridodecylchlorosilane and octadecyltrichlorosilane (OTS). Silylation of the glass surface renders the reacted portion of the surface plastic-like. The inside tube wall may be modified to be plastic like at either the open end or preferably at the closed end of the tube. Example I provides experimental details for this aspect of the invention.

In a second embodiment of the invention, a plastic tube may be treated to have a glass like region on its interior surface. The glass-like region may be introduced at either the closed end of the tube or preferably at the open end.

The plastic tube may be of any polymer which can be treated to have a glass-like surface region. Representative polymers are, for example, polyethylene terephthalate, polyethylene, polypropylene, polytetrafluoroethylene, polysiloxane, polyvinyl chloride and preferably polystyrene (PS).

Suitable reagents for this embodiment of the invention are chromic acid and preferably sulfuric acid whereby the polymer structure is attacked by the acid with introduction of polar groups.

The most preferred tube of the invention is a polystyrene blood collection tube treated with sulfuric acid to have a glass like surface near the tube mouth to enhance the clotting sequence without clot adherence and the native plastic surface in the area near the closed end to enhance adherence of the clot at the bottom of the tube during centrifugation. This tube is easily made by immersion of the open end of the polystyrene tube in the sulfuric acid solution, as described in detail in Example II.

From the above disclosure of suitable methods to achieve surface regions of different surface chemistry, it will be apparent that the regions of modified chemistry can be of any size depending merely on how much reagent is added to the tube for bottom-end treatment or how far the mouth of the tube is inserted into the reagent for top end treatment. Thus the glass-like surface region may be from about 10-75, preferably about 50 to 60% of the inside wall surface with the remainder of the surface being plastic like.

While the invention has been described in detail for a tube, particularly a blood collection tube, it is evident that other articles may benefit from a plurality of surface regions. For example, a tissue being cultured in a culture bottle, flask or dish may behave differently when the surface has both glass-like and plastic like regions.

EXAMPLE I

A hydrophobic, plastic-like region on glass disposable culture tubes (10 mm × 75 mm, Corning Glass Works) was created by carefully pipetting a 2% chloroform solution of OTS into the tube. The total height of the plastic-like region was varied by varying the total volume of OTS solution. Reaction between glass and OTS was allowed to proceed for about 15 minutes at room temperature after which the reactants were aspirated from the tube. Tubes were sequentially rinsed by serial addition and aspiration of chloroform to remove all unreacted OTS. Observation of the shape of water droplets along the tube axis confirmed that the treated region was hydrophobic. The tubes were filled with 4.5 ml of citrated porcine blood containing 0.1 molar calcium chloride and incubated for 30 min at 37° C. to allow blood to clot. The tubes were then centrifuged under standard hematological conditions (1380 G, 3300 rpm).

The character and position of blood clots relative to the hydrophobic surface region were noted. It was observed that the position of clot adherence along the tube axis positively correlated with the position of the hydrophobic region and that the clot was strongly adherent to this layer. Clots in control glass tubes without the hydrophobic, plastic-like region were observed to be pulled away from the wall of the tube wall in a non-adherent manner. These experiments illustrate the adherence of clotted blood to a plastic like hydrophobic region in a tube comprised of an inherently hydrophilic material to which blood clots do not adhere.

EXAMPLE II

Glass tubes with plastic-like hydrophobic regions of various length in the upper portion of the tube were created by allowing the OTS solution of Example I to contact only the upper portion of the tube. This was accomplished by tilting and rolling the tube while pipetting the OTS solution into the tube, so that only the selected portion was in contact with the silane reagent. Tubes were sequentially rinsed by serial addition and aspiration of chloroform to remove all unreacted OTS. Observation of the shape of water droplets along the tube axis confirmed that the treated region was hydrophobic after tubes were air dried. Blood was clotted and centrifuged in these treated tubes and untreated control tubes as described in Example I. Blood clot was observed to adhere to the hydrophobic region in each case, including those in which the hydrophobic region was within the upper 25-50% of the tube. By contrast, clot did not adhere to untreated glass surfaces or that of untreated control glass tube. These experiments show that adhesion forces between the blood clot and hydrophobic regions exceed the stress of centrifugal forces in a hematology centrifuge, verifying the mechanical integrity of a clot adhered to plastic-like regions in a glass tube and resistance to remixing into the serum.

EXAMPLE III

Polystyrene culture tubes (Becton Dickinson 12×75 mm) were treated with a radio frequency oxygen plasma (30 Watts 13.56 MHz, planar diode system held at 250 millitorr oxygen) to oxidize the entire interior and exterior surface of the tubes and produce a glass-like surface treatment. Another set of these plastic tubes were filled with concentrated sulfuric acid to sulfonate the aromatic ring of the polystyrene. After 30 minutes reaction at room temperature, sulfonated tubes were rinsed with copious amounts of distilled water and air dried. Observation of the shape of water droplets along the tube axis confirmed that the treated region was a hydrophilic, water-wettable surface. Blood was allowed to clot in these tubes as described in Example I. It was observed that blood clot did not adhere to the inside wall of the plasma oxidized and sulfonated tubes, behaving in an identical fashion to that of glass control tubes. These experiments verify that surface treatments that render plastic surfaces water-wettable confer a glass-like property with respect to clot adhesion to plastic surfaces.

EXAMPLE IV

Sulfuric acid was carefully added with a pipette into the lower portion of polystyrene tubes in a manner similar to that described in Example I using OTS. In this case, however, the lower portions of the tubes were rendered hydrophilic rather than hydrophobic as in Example I. The character of blood clots and position relative to the hydrophobic surface region were noted as described in Example I. It was observed that the position of clot adherence along the tube axis positively correlated with the position of the hydrophobic, untreated region on the tube and that the clot was strongly adherent to this layer and did not pellet during centrifugation as described in Example II. Clots on sulfonated region were observed to be pulled away from the wall of the tube wall in a non-adherent manner as in Example III. These experiments illustrate the non-adherence of clotted blood to a glass like hydrophilic region in a tube of an inherently hydrophobic material to which blood clots do adhere.

Examples I-IV show that clot position and adherence within a tube can be controlled by surface treatments that produce plastic like or glass-like properties, respectively.

What is claimed is:

1. An article comprising a wall having a wall surface, said wall surface having a plurality of surface regions, a first of said surface regions being substantially glass-like and promoting clotting of blood and a second of said surface regions being substantially plastic-like and adhering to clotted blood.

2. The article of claim 1 which is a plastic film.

3. The article of claim 1 which is a glass plate.

4. An article having an open end, a closed end, a side wall and a bottom wall, said side wall and bottom wall defining an inside wall surface, said inside wall surface having a first surface region which is substantially glass-like and which promotes clotting of blood, and a second surface region which is substantially plastic-like and which adheres to clotted blood.

5. The article of claim 4 which is a tube.

6. The article of claim 4 which is a flask.

7. The article of claim 4 which is a dish.

8. The article of claim 4 which is glass, said first region being the native glass surface and said second region being the glass surface after being modified to be plastic-like.

9. The article of claim 4 which is plastic, aid first region being the plastic surface after being modified to be glass-like and said second region being the native plastic surface.

10. The article of claim 9 wherein said plastic is selected from the group consisting of polyethylene, polypropylene, polytetrafluoroethylene, polyvinyl chloride, polyethylene terephthalate, polysiloxane and polystyrene.

11. A plastic tube comprising an open end, a closed end a side wall and a bottom wall, said side wall and bottom wall defining an inside wall surface, a region of said inside wall surface adjacent said open end having surface chemistry which is substantially glass-like and which promotes clotting of blood and a region of said inside wall surface adjacent said bottom wall having a surface chemistry which is substantially plastic-like and which is adherent to clotted blood.

12. The tube of claim 11 which is polystyrene, said region adjacent said open end being the polystyrene surface after being modified to be glass-like and said surface adjacent said bottom wall being the native polystyrene surface.

13. The tube of claim 11 further comprising a septum over said open end.

* * * * *